US010934367B2

(12) United States Patent
Yoshida et al.

(10) Patent No.: US 10,934,367 B2
(45) Date of Patent: Mar. 2, 2021

(54) HYPROMELLOSE ACETATE SUCCINATE AND METHOD FOR PRODUCING HYPROMELLOSE ACETATE SUCCINATE

(71) Applicant: SHIN-ETSU CHEMICAL CO., LTD., Tokyo (JP)

(72) Inventors: Mitsuhiro Yoshida, Joetsu (JP); Junichi Matsubara, Joetsu (JP); Kazuki Kikuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 70 days.

(21) Appl. No.: 15/683,222

(22) Filed: Aug. 22, 2017

(65) Prior Publication Data

US 2018/0057612 A1 Mar. 1, 2018

(30) Foreign Application Priority Data

Aug. 29, 2016 (JP) ............................ JP2016-166956

(51) Int. Cl.

| | |
|---|---|
| ***C08B 3/06*** | (2006.01) |
| ***C08B 13/00*** | (2006.01) |
| ***A61K 47/38*** | (2006.01) |
| ***B04B 1/20*** | (2006.01) |

(52) U.S. Cl.

CPC ................ *C08B 3/06* (2013.01); *A61K 47/38* (2013.01); *B04B 1/20* (2013.01); *C08B 13/00* (2013.01)

(58) Field of Classification Search

CPC .............. C08B 13/00; C08B 3/06; C08B 3/16

USPC .......................... 536/124, 66, 64, 69, 90, 91

See application file for complete search history.

(56) References Cited

U.S. PATENT DOCUMENTS

| | | | |
|---|---|---|---|
| 4,398,024 A | 8/1983 | Bernert et al. | |
| 9,453,081 B2 * | 9/2016 | Sprehe .................... | C08B 13/00 |
| 2015/0044289 A1 | 2/2015 | Maruyama et al. | |

FOREIGN PATENT DOCUMENTS

| | | |
|---|---|---|
| CN | 104558208 A * | 4/2015 |
| EP | 2837391 A1 | 2/2015 |
| JP | 2007-233016 A | 9/2007 |
| JP | 2015-057380 A | 3/2015 |
| WO | 97/40941 A1 | 11/1997 |
| WO | 2015/041973 A1 | 3/2015 |

OTHER PUBLICATIONS

Chen et al, CN 1045582085 A, China, Machine Translated Copy, Apr. 2015,. (Year: 2015).*

Dec. 21, 2017 Search Report issued in European Patent Application No. 17187808.5.

Aug. 19, 2019 Office Action issued in Japanese Patent Application No. 2016-166956.

* cited by examiner

*Primary Examiner* — Shaojia A Jiang
*Assistant Examiner* — Everett White
(74) *Attorney, Agent, or Firm* — Oliff PLC

(57) ABSTRACT

Provided is a method for producing HPMCAS capable of reducing the average particle size of HPMCAS particles to an intended range without a pulverization step. Specifically provided is a method for producing hypromellose acetate succinate, comprising an esterification step of reacting hypromellose with an esterification agent in the presence of a catalyst to obtain a reaction solution containing crude hypromellose acetate succinate, a precipitation step of mixing the reaction solution with water to precipitate the crude hypromellose acetate succinate, thereby obtaining a hypromellose acetate succinate suspension, a liquid removal step of removing a liquid from the hypromellose acetate succinate suspension with a centrifugal decanter to obtain liquid-removed hypromellose acetate succinate, and a drying step of drying the liquid-removed hypromellose acetate succinate.

16 Claims, 1 Drawing Sheet

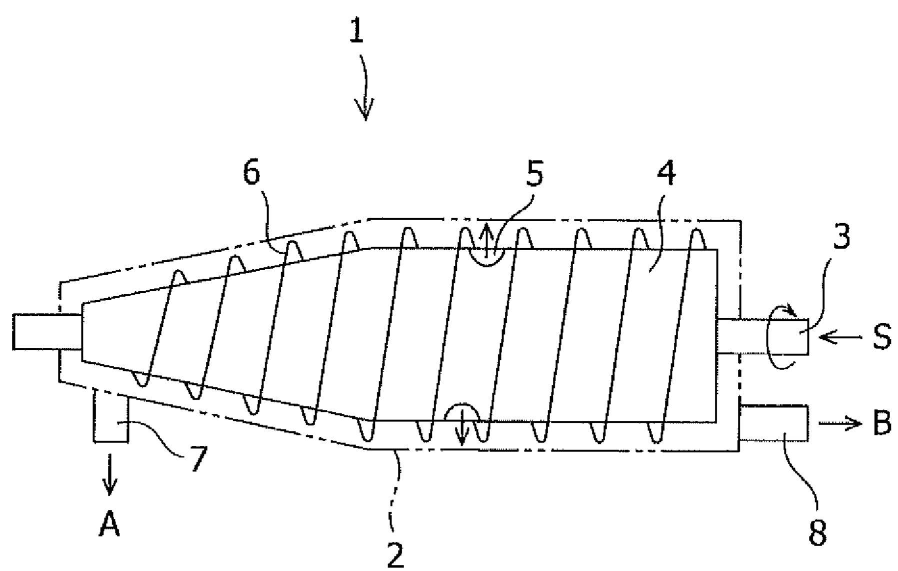
1
6
5
4
3
S
B
7
A
2
8

HYPROMELLOSE ACETATE SUCCINATE AND METHOD FOR PRODUCING HYPROMELLOSE ACETATE SUCCINATE

BACKGROUND OF THE INVENTION

1. Field of the Invention

The invention relates to hypromellose acetate succinate and a method for producing hypromellose acetate succinate.

2. Related Art

As an enteric polymer, hypromellose acetate succinate (hereinafter also called "HPMCAS"), which is a polymer having four types of substituents in total, is widely known, and is produced by substituting the hydrogen atoms of hydroxy groups on a cellulose skeleton with two substituents of a methyl group ($—CH_3$) and a hydroxypropyl group ($—C_3H_6OH$) to obtain an ether structure, as well as with two substituents of an acetyl group ($—COCH_3$) and a succinyl group ($—COC_2H_4COOH$) to obtain an ester structure.

The HPMCAS is used for a wide range of applications such as applications of coating, drug release control, and production of a solid dispersion through hot melt extrusion or spray drying of HPMCAS together with a poorly water-soluble drug. The hot melt extrusion can eliminate the use of a solvent so that it can be applied to a drug unstable in water. Thus, the hot melt extrusion has been drawing attention in terms of safety due to the unnecessity of solvent recovery, reduction of environmental concerns, saving of energy in a solvent recovery process, and improvement in safety of operators.

In the production of a solid dispersion through the hot melt extrusion, the flowability of HPMCAS powder and the miscibility thereof with a drug are important to stably produce a hot melt extrudate having an excellent uniform distribution of a carrier (HPMCAS) and a drug. It is proposed as a method for producing HPMCAS for a hot melt extrudate that dried granules of HPMCAS are pulverized with a pulverizer to adjust the average particle size thereof to a certain range (70 to 300 μm) (JP 2015-57380A).

SUMMARY OF THE INVENTION

However, dried HPMCAS is a heat-sensitive material having a low softening temperature so that the particles thereof are fusion-bonded with each other by heat generated during pulverization and adhere to the inside of a pulverizer. To suppress the fusion and adhesion, a pulverizer having such a structure as to be unlikely to increase the temperature of a material (e.g. an impact grinder or a jet mill in which the content therein can be cooled by a large amount of air or the like) is required, but a dried HPMCAS pulverized with such a pulverizer is likely to have an excessively small particle size.

In view of the above circumstances, an object of the invention is to provide a method for producing HPMCAS capable of reducing the average particle size of HPMCAS particles to an intended range without a pulverization step.

As a result of intensive studies for achieving the object, the inventors have surprisingly found that the average particle size of particles suspended in the suspension of HPMCAS can be reduced without a pulverization step, by using a method comprising the steps of: reacting hypromellose with an esterification agent, mixing the resulting reaction solution with water to obtain a suspension containing precipitated crude hypromellose acetate succinate, and subjecting the suspension to liquid removal (solid-liquid separation) with a centrifugal decanter (also called "decanter type centrifugal separator").

In an aspect of the invention, there is provided a method for producing hypromellose acetate succinate, comprising an esterification step of reacting hypromellose with an esterification agent in a presence of a catalyst to obtain a reaction solution containing crude hypromellose acetate succinate, a precipitation step of mixing the reaction solution with water to precipitate the crude hypromellose acetate succinate, thereby obtaining a hypromellose acetate succinate suspension, a liquid removal step of removing a liquid from the hypromellose acetate succinate suspension with a centrifugal decanter to obtain liquid-removed hypromellose acetate succinate, and a drying step of drying the liquid-removed hypromellose acetate succinate.

In another aspect of the invention, there is provided hypromellose acetate succinate having an average particle size, determined by dry laser diffractometry, of 70 to 300 μm and a compressibility of 20% or less.

According to the invention, the average particle size of HPMCAS particles can be reduced to an intended range without a pulverization step of using a pulverizer. In the particle size reduction of heat-sensitive material HPMCAS, this method enables the production of HPMCAS having an intended average particle size without restriction of a pulverizer. In addition, the average particle size of suspended particles can be reduced concurrently with the liquid removal of the HPMCAS suspension, so that the production process is simplified to reduce the facility cost. Moreover, the liquid-removed HPMCAS has a smaller average particle size so that the drying time is shortened to improve the productive capacity.

BRIEF DESCRIPTION OF THE DRAWINGS

FIG. 1 is a schematic view of an example of the centrifugal decanter to be used for removing a liquid from a hypromellose acetate succinate suspension.

DETAILED DESCRIPTION OF THE PREFERRED EMBODIMENTS

Hypromellose (another name: hydroxypropyl methyl cellulose, hereinafter also called "HPMC") as the starting material may be a commercial product or may be produced by a known method. For example, a known method comprises the steps: bringing a pulp in the form of sheet, chips, or powder into contact with a solution of alkali metal hydroxide such as sodium hydroxide and potassium hydroxide to obtain alkali cellulose, and reacting the alkali cellulose with an etherifying agent such as methyl chloride and propylene oxide to obtain the hypromellose.

The alkali metal hydroxide solution to be used may be any solution that can produce alkali cellulose. It is preferably an aqueous solution of sodium hydroxide or potassium hydroxide from the standpoint of economy. The concentration thereof is preferably 23 to 60% by weight, more preferably 35 to 55% by weight from the standpoint of the stable formulation of alkali cellulose and keeping of the transparency of a cellulose ether.

After the step of producing alkali cellulose, the alkali cellulose is reacted with an etherifying agent such as methyl chloride and propylene oxide for an etherification reaction to obtain HPMC in a usual manner.

The obtained HPMC preferably has a methoxy substitution degree of 28.0 to 30.0% by weight, more preferably 28.8 to 29.2% by weight. A hydroxypropoxy substitution degree is preferably 8.5 to 10.0% by weight, more preferably 8.8 to 9.2% by weight. The methoxy substitution degree and the hydroxypropoxy substitution degree can be determined, for example, by an analytical method for hypromellose in the Japanese Pharmacopoeia Seventeenth Edition.

The viscosity at 20° C. of a 2% by weight aqueous HPMC solution is determined in accordance with the viscosity measurement by capillary tube viscometer in the Japanese Pharmacopoeia Seventeenth Edition. It is preferably 2.2 to 7.2 mPa·s, more preferably 3.0 to 3.5 mPa·s.

The above-produced or commercially available HPMC can be used to produce HPMCAS through an esterification step, a precipitation step, an optional washing step, a liquid removal step, and a drying step.

In the esterification step, HPMC is reacted with an esterification agent (e.g. succinic anhydride and acetic anhydride) in the presence of a catalyst to obtain a reaction solution.

The solvent to be used for the esterification is preferably a solvent capable of dissolving the HPMC, the esterification agent and the catalyst. It is, for example, not water, but glacial acetic acid. The amount of the solvent to be used is preferably 1.0 to 3.0 times, more preferably 1.2 to 2.0 times, even more preferably 1.5 to 1.8 times the weight of the HPMC from the standpoint of reaction rate.

The catalyst to be used in the esterification step is preferably an alkali metal carboxylate such as sodium acetate from the standpoint of economy. The amount of the catalyst is preferably 0.1 to 1.5 times, more preferably 0.6 to 1.1 times the mole of the reactant HPMC from the standpoint of the composition and yield.

The amount of succinic anhydride is preferably 0.1 to 1.0 times, more preferably 0.3 to 0.5 times the mole of the reactant HPMC from the standpoint of the composition and yield. The amount of acetic anhydride is preferably 0.2 to 1.5 times, more preferably 1.1 to 1.3 times the mole of the reactant HPMC from the standpoint of the composition and yield.

For the esterification, a biaxial mixer suited for forming and kneading a uniform mixture which is a highly viscous fluid, may be used. More specifically, a commercially available mixer including what is called a kneader or an internal mixer may be used.

The reaction temperature in the esterification step is preferably 60 to 100° C., more preferably 80 to 90° C. from the standpoint of reaction rate or viscosity increase. The reaction time in the esterification step is preferably 2 to 8 hours, more preferably 3 to 6 hours.

After the esterification, water may be added to the reaction solution to decompose unreacted succinic anhydride and acetic anhydride. The amount of water is preferably 0.8 to 1.5 times, more preferably 1.0 to 1.3 times the weight of the HPMC.

In the precipitation step, the obtained reaction solution is mixed with water to precipitate crude HPMCAS, thereby obtaining an HPMCAS suspension. The amount of water is preferably 8.0 to 50.0 times, more preferably 12.0 to 35.0 times the weight of the HPMC from the standpoint of precipitation degree and treatment time. The temperature of water to be brought into contact is preferably 0 to 40° C., more preferably 0 to 30° C. The temperature of the reaction solution immediately before being mixed with water is preferably 10 to 80° C., more preferably 10 to 50° C.

The resulting HPMCAS suspension contains impurities including salts, free acetic acid and free succinic acid. Since a centrifugal decanter (decanter type centrifugal separator) can be expected to provide a washing effect, the obtained HPMCAS suspension without any treatment can be subjected to liquid removal by using the centrifugal decanter (decanter type centrifugal separator). Alternatively, an optional washing step may be introduced between the precipitation step and the liquid removal step. In the washing step, crude HPMCAS in the HPMCAS suspension obtained in the precipitation step is washed to give a hypromellose acetate succinate suspension to be used in the liquid removal step.

Typically, the washing may be carried out by using a filtration apparatus such as a batch type stirring filtration apparatus, a continuous type rotary pressure filtration apparatus, a continuous type horizontal vacuum filtration apparatus, a horizontal table filtration apparatus, and a horizontal belt filtration apparatus. In the washing step, for example, water is used to wash crude HPMCAS. When the washing step is carried out, a decanter is used mainly for liquid removal.

After the precipitation step or after the optional washing step following the precipitation step, a liquid removal step of removing a liquid with a centrifugal decanter (decanter type centrifugal separator) is carried out. By using the centrifugal decanter (decanter type centrifugal separator) for liquid removal (solid-liquid separation) of the suspension of the crude HPMCAS or the HPMCAS obtained in the washing step, it has been surprisingly found that the particle size of suspended particles (i.e. particles of the crude HPMCAS or the HPMCAS obtained in the washing step) in the suspension can be reduced concurrently with the liquid removal. In other words, a conventional method comprising, after washing, dehydration with a dehydrator such as a pressure dehydrator, a vacuum dehydrator, a centrifugal dehydrator and a compression dehydrator, drying of a dehydrated substance, and pulverization of the dried substance with a pulverizer for reduction of particle size, can be changed so that the production efficiency can be improved.

The centrifugal decanter (decanter type centrifugal separator) is an apparatus typically for separating a suspension into a solid and a liquid (i.e. solid-liquid separation of a suspension) by centrifugal force. The centrifugal decanter comprises an outer rotary cylinder having a substantially cylindrical shape with a small inner diameter at one of the longitudinal direction ends of the cylinder, and being rotatable at a high speed; and a screw conveyor concentrically provided inside the outer rotary cylinder. The screw conveyor comprises a cylinder-shaped screw barrel, screw blades fixed on the outer circumference surface of the cylinder-shaped screw barrel, and a suspension-feeding pipe for feeding a suspension between the outer circumference surface of the screw barrel and the inner circumference surface of the outer rotary cylinder. The screw conveyor is rotated at a high speed which differs from a rotation speed of the outer rotary cylinder. The outer rotary cylinder comprises a discharge port for discharging a separated solid at one end with a small inner diameter in the longitudinal direction of the cylinder to the outside of the apparatus, and a drainage port for draining a separated liquid (clear liquid) at the other end in the longitudinal direction of the cylinder to the outside of the apparatus. Examples of the centrifugal decanter include a screw decanter type centrifugal separator (manufactured by IHI Corporation), a decanter type continuous centrifugal separator (manufactured by TANABE WILLTEC INC.), and a high efficiency screw decanter (manufactured by SAITO SEPARATOR LIMITED).

A method of removing a liquid from an HPMCAS suspension with the centrifugal decanter will be described on basis of the centrifugal decanter exemplified in FIG. 1. First, a centrifugal decanter (decanter type centrifugal separator) 1 is driven to rotate an outer rotary cylinder 2. After an intended centrifugal effect is attained, a suspension S is fed through a suspension-feeding pipe 3 into a screw barrel 4. The suspension S fed into the screw barrel 4 is introduced from outlets 5 of the suspension-feeding pipe into the outer rotary cylinder 2 rotating at a high speed, and a solid (suspended particles) A having a large specific gravity is settled and separated by centrifugal force onto the inner wall of the outer rotary cylinder 2. The solid A settled on the inner wall of the outer rotary cylinder 2 sequentially moves in the direction of a discharge port 7 at an end of the outer rotary cylinder 2 by a screw conveyor 6 which rotates at a rotation speed slightly different from that of the outer rotary cylinder 2 on the same axis, undergoes liquid removal by centrifugal force on the slope toward the discharge port 7, and is discharged through the discharge port 7 to the outside of the apparatus. The particle size of the solid (suspended particles) A in the suspension S is reduced in the process between the feeding into the outer rotary cylinder 2 and the discharge to the outside of the apparatus, and as a result, the suspended particles have a smaller average particle size. The liquid B separated by centrifugation flows in the direction opposite to the solid and is drained through a drainage port 8 to the outside of the apparatus.

The suspended particles in an HPMCAS suspension to be fed into the centrifugal decanter preferably have an average particle size of 150 μm or more, more preferably 150 to 4,000 μm, even more preferably 150 to 2,000 μm, particularly preferably 150 to 1,000 μm from the standpoint of a reduction ratio of the particle size or the like.

The concentration of a suspension (i.e. weight proportion of suspended particles per unit weight of suspension) to be fed into the centrifugal decanter is not particularly limited, and is preferably 20% by weight or less, more preferably 15% by weight or less from the standpoint of, for example, cohesiveness of particles. The lower limit of the concentration of the suspension is not particularly limited, and is 0.1% by weight from the standpoint of productivity or the like.

When the HPMCAS suspension obtained in the precipitation step is fed into the centrifugal decanter without the washing step, the HPMCAS suspension may be optionally adjusted to a preferred concentration before being fed into the centrifugal decanter. When the HPMCAS suspension obtained in the precipitation step is subjected to the washing step by using, for example, a filtration device before being fed into the centrifugal decanter, the HPMCAS obtained in the washing step may be mixed with water and optionally adjusted to a preferred concentration, and the resulting HPMCAS suspension may be fed into the centrifugal decanter.

The temperature of the suspension to be fed into the centrifugal decanter is not particularly limited, and is preferably 80° C. or less, more preferably 60° C. or less, even more preferably 40° C. or less from the standpoint of, for example, cohesiveness of particles. The lower limit of the temperature of the suspension is not particularly limited, and is preferably 0° C. from the standpoint of operability or the like.

A reduction ratio, which is the ratio of the decreased average particle size of the HPMCAS liquid-removed with the centrifugal decanter to the average particle size of the suspended particles in the HPMCAS suspension to be fed into the centrifugal decanter is preferably 10 to 90%, more preferably 20 to 80% from the standpoint of efficient production or the like. More specifically, when the suspended particles in the HPMCAS suspension have an average particle size of 150 to 300 μm, the reduction ratio is 10 to 30%, and when the suspended particles in the HPMCAS suspension have an average particle size of 300 μm or more, the reduction ratio is 30 to 90%. In other words, the "reduction ratio" means a reduction ratio of the average particle size of suspended particles after the liquid removal to the average particle size of suspended particles before the liquid removal, and is calculated by the following equation:

Reduction ratio(%)={1−(average particle size after liquid removal/average particle size before liquid removal)}×100.

As the average particle size of the suspended particles in the suspension before the liquid removal and the average particle size after the liquid removal, a particle size at an integrated value of 50% in a weight integral particle size distribution by a sieve analysis is used.

The liquid-removed HPMCAS after the liquid removal with a centrifugal decanter preferably has an average particle size of 70 to 400 μm, more preferably 80 to 300 μm, even more preferably 100 to 300 μm from the standpoint of, for example, operability and drying efficiency.

The centrifugal effect of a centrifugal decanter in operation is preferably 500 G or more, more preferably 600 G or more, even more preferably 900 G or more from the standpoint of, for example, the reduction ratio of suspended particles, a liquid content of a solid after the liquid removal, and a solid concentration (loss ratio) in a separated liquid. The upper limit of the centrifugal effect is not particularly limited, and is, for example, 5,000 G. The "centrifugal effect" is an index indicating the intensity of centrifugal force applied to a suspension, and is defined by the following equation:

$$\text{Centrifugal effect}\,G(-)=N^2\cdot r/894,$$

wherein N is the number of rotations per minute of an outer rotary cylinder, and r is an inner radius (unit: m) of the outer rotary cylinder.

The liquid content of suspended particles after the liquid removal is not particularly limited, and is preferably 90% by weight or less, more preferably 80% by weight or less, even more preferably 70% by weight or less from the standpoint of drying efficiency or the like. The lower limit of the liquid content of suspended particles after the liquid removal is not particularly limited, and is, for example, 5% by weight. The liquid content of suspended particles can be determined by Loss on Drying Test in General Tests of the Japanese Pharmacopoeia Seventeenth Edition.

In the drying step, the HPMCAS cake obtained in the liquid removal step is dried to an intended water content (for example, 0.1 to 5.0% by weight). The drying temperature is not particularly limited, and is preferably normal temperature (20±15° C.) to 120° C., more preferably 50° C. to 90° C. from the standpoint of, for example, drying capacity and discoloration (quality) of a dried product. A dryer is not particularly limited, and examples thereof include a vacuum drier, a fluidized-bed dryer, and a flash dryer.

The dried HPMCAS obtained as above preferably has an average particle size of 70 to 300 μm, more preferably 70 to 280 μm, even more preferably 70 to 250 μm from the standpoint of powder flowability and miscibility with a drug. The average particle size of a dried product can be determined by dry laser diffractometry (for example, with a MASTERSIZER manufactured by Malvern Instruments Ltd in England).

Next, the compressibility, the loose bulk density, the packed bulk density, and the repose angle of the dried HPMCAS obtained as above will be described.

The compressibility is preferably 20% or less, more preferably 18% or less. The dried HPMCAS having a compressibility of more than 20% is, for example, likely to form bridges in a feed hopper and may not be stably fed. The lower limit of the compressibility is not particularly limited, and is preferably 0% from the standpoint of flowability.

The compressibility is a value indicating the degree of bulk reduction and can be calculated by the following equation:

Compressibility(%)={(packed bulk density−loose bulk density)/packed bulk density}×100.

The compressibility is considered to be a numerical value representing the flowability of powder.

The loose bulk density is preferably 0.1 to 0.6 g/cm$^3$, more preferably 0.2 to 0.5 g/cm$^3$ from the standpoint of facility cost or handleability.

The "loose bulk density" is a bulk density in a loosely packed state and is determined by the method comprising the steps of: evenly placing sample powder which has passed through a 24-mesh sieve, into a cylindrical container with a diameter of 5.03 cm and a height of 5.03 cm (a capacity of 100 ml) from 23 cm above the cylindrical container; leveling off the sample powder at the top surface of the container; and then weighing the sample powder.

The packed bulk density is preferably 0.1 to 0.7 g/cm$^3$, more preferably 0.2 to 0.6 g/cm$^3$ from the standpoint of facility cost or handleability.

The "packed bulk density" is a bulk density of closely packed sample powder by tapping the sample powder after the measurement of the "loose bulk density". The tapping is an operation in which a container filled with the sample powder is repeatedly dropped from a predetermined height to apply a small impact to the bottom for closely packing the sample powder. In practice, after the sample powder is leveled off at the top surface of the container and is weighed to determine the loose bulk density, a cap is attached to the top of the container; sample powder is further added to the upper end of the inside of the cap; and the whole is tapped 180 times from a height of 1.8 cm. After the completion of the tapping, the cap is detached, and then the sample powder is leveled off at the top surface of the container and is weighed. The bulk density in this state is regarded as the packed bulk density. The "packed bulk density" and the "loose bulk density" can be measured by using a powder tester manufactured by Hosokawa Micron Corporation.

The repose angle is preferably 45° or less, more preferably 40° or less from the standpoint of flowability.

The repose angle is an angle between the generating line of a cone formed by dropping and piling sample powder onto a flat surface and the horizontal plane. For example, a powder tester, type PT-D (manufactured by Hosokawa Micron Corporation) is used to feed sample powder onto a round metal table having a diameter of 80 mm from a height of 75 mm until a constant angle is attained, and the angle between the piled sample powder and the table is measured to determine the repose angle. Powder having a smaller repose angle is considered to have excellent flowability.

EXAMPLES

The invention will next be described in detail with reference to Examples and Comparative Examples. It should not be construed that the invention is limited to or by Examples.

Example 1

The 6.0 kg of hydroxypropyl methyl cellulose having a hydroxypropoxy substitution degree per glucose unit of 9.0% by weight and a methoxy substitution degree per glucose unit of 28.9% by weight was added to 9.6 kg of glacial acetic acid in a 50-L kneader with a biaxial mixer, dissolved, then subjected to addition of 1.7 kg of succinic anhydride, 3.2 kg of acetic anhydride and 2.9 kg of sodium acetate, and reacted at 85° C. for 5 hours. The reaction mixture was subjected to addition of 6.7 kg of water and stirred. Then, water in an amount of 20 times the weight of the HPMC was gradually added to the reaction solution to precipitate crude HPMCAS. The precipitate was filtered by using a horizontal filter plate type filtration device and washed with water. The obtained HPMCAS was mixed with water to obtain a suspension having a temperature of 13° C. and an HPMCAS concentration of 6% by weight. The HPMCAS suspended particles in the obtained suspension had an average particle size of 615 μm, which was measured as a particle size at an integrated value of 50% in a weight integral particle size distribution determined from the ratios of suspended particles passing through nine sieves having different sieve openings.

The HPMCAS suspension was subjected to liquid removal (solid-liquid separation) by using a centrifugal decanter (decanter type continuous centrifugal separator, type Z18, manufactured by TANABE WILLTEC INC.) at a centrifugal effect of 2500 G. After the liquid removal, the HPMCAS suspended particles had an average particle size of 178 μm, and the reduction ratio of 71%. After the liquid removal, the HPMCAS cake had a liquid content of 65.1% by weight.

Next, the obtained HPMCAS cake was dried by using a fluidized-bed dryer at 80° C. The drying time of the HPMCAS cake was 0.68 relative to the drying time of the liquid-removed HPMCAS cake in Comparative Example 1 after liquid removal by using a filtration type centrifugal dehydrator. The results are shown in Table 1.

The dried HPMCAS was then sieved through a 10-mesh sieve (sieve opening of 1700 μm), and the average particle size by dry laser diffractometry was determined to be 160 μm, which satisfied an intended average particle size of 100 to 200 μm.

Various powder properties of the HPMCAS after sieving were determined, and the results are shown in Table 2.

By using the centrifugal decanter, not only the average particle size of the HPMCAS was reduced, but also the drying time was shortened. The obtained HPMCAS had a compressibility of 20% or less, indicating high flowability.

Comparative Example 1

The HPMCAS suspension obtained in Example 1 was subjected to liquid removal (solid-liquid separation) by using a filtration type centrifugal dehydrator (upper discharge type centrifugal separator, type H-130A, manufactured by KOKUSAN Co., Ltd.) at a centrifugal effect of 1200 G in place of the centrifugal decanter. After the liquid removal, the HPMCAS particles had an average particle size of 596 μm and the reduction ratio was 3%. After the liquid removal, the HPMCAS cake had a liquid content of 66.0% by weight. The results are shown in Table 1.

The HPMCAS cake was dried at 80° C. in the same manner as in Example 1, then sieved through a 10-mesh sieve (sieve opening of 1700 μm), and the average particle size by dry laser diffractometry was determined to be 477 μm, which was larger than an intended average particle size of 100 to 200 μm.

Various powder properties of the HPMCAS after sieving were determined, and the results are shown in Table 2.

Example 2

An HPMCAS suspension having a temperature of 13° C., a concentration of 6% by weight and an average particle size of suspended particles of 615 μm, was obtained in the same manner as in Example 1. The HPMCAS suspension was subjected to liquid removal (solid-liquid separation) by using a centrifugal decanter (decanter type continuous centrifugal separator, type Z18, manufactured by TANABE WILLTEC INC.) at a centrifugal effect 900 G. After the liquid removal, the HPMCAS particles had an average particle size of 343 μm and the reduction ratio was 44%. After the liquid removal, the HPMCAS cake had a liquid content of 66.4% by weight.

The HPMCAS cake was dried at 80° C. in the same manner as in Example 1. The drying time of the HPMCAS cake was 0.95 relative to the drying time of the liquid-removed HPMCAS cake in Comparative Example 1 after the liquid removal by using a filtration type centrifugal dehydrator. The results are shown in Table 1.

The dried HPMCAS was then sieved through a 10-mesh sieve (sieve opening of 1700 μm), and the average particle size by dry laser diffractometry was determined to be 295 μm, which satisfied an intended average particle size of 200 to 300 μm. The result is shown in Table 2.

Various powder properties of the HPMCAS after sieving were determined, and the results are shown in Table 2.

Example 3

An HPMCAS suspension having a temperature of 13° C., a concentration of 6% by weight and an average particle size of suspended particles of 494 μm, was obtained in the same manner as in Example 1 except that the washing step of washing a crude HPMCAS was not carried out. The HPMCAS suspension was subjected to liquid removal (solid-liquid separation) by using a centrifugal decanter (decanter type continuous centrifugal separator, type Z18, manufactured by TANABE WILLTEC INC.) at a centrifugal effect of 2500 G. After the liquid removal, the HPMCAS particles had an average particle size of 196 μm and the reduction ratio was 60%. After the liquid removal, the HPMCAS cake had a liquid content of 64.9% by weight.

The HPMCAS cake was dried at 80° C. in the same manner as in Example 1. The drying time of the HPMCAS cake was 0.72 relative to the drying time of the liquid-removed HPMCAS cake in Comparative Example 1 after liquid removal by using a filtration type centrifugal dehydrator. The results are shown in Table 1.

The dried HPMCAS was then sieved through a 10-mesh sieve (sieve opening of 1700 μm), and the average particle size by dry laser diffractometry was determined to be 174 μm, which satisfied an intended average particle size of 100 to 200 μm. The result is shown in Table 2.

Various powder properties of the HPMCAS after sieving were determined, and the results are shown in Table 2.

Example 4

An HPMCAS suspension having a temperature of 13° C., a concentration of 6% by weight and an average particle size of suspended particles of 209 μm, was obtained in the same manner as in Example 1. The HPMCAS suspension was subjected to liquid removal (solid-liquid separation) by using a centrifugal decanter (decanter type continuous centrifugal separator, type Z18, manufactured by TANABEW WILLTEC INC.) at a centrifugal effect of 2500 G. After the liquid removal, the HPMCAS particles had an average particle size of 149 μm and the reduction ratio was 29%. After the liquid removal, the HPMCAS cake had a liquid content of 64.2% by weight.

The HPMCAS cake was dried at 80° C. in the same manner as in Example 1. The drying time of the HPMCAS cake was 0.63 relative to the drying time of the liquid-removed HPMCAS cake in Comparative Example 1 after liquid removal by using a filtration type centrifugal dehydrator. The results are shown in Table 1.

The dried HPMCAS was then sieved through a 10-mesh sieve (sieve opening of 1700 μm), and the average particle size by dry laser diffractometry was determined to be 131 μm, which satisfied an intended average particle size of 100 to 200 μm. The result is shown in Table 2.

Various powder properties of the HPMCAS after sieving were determined, and the results are shown in Table 2.

Example 5

An HPMCAS suspension having a temperature of 13° C., a concentration of 6% by weight and a suspended particle average particle size of 260 μm, was obtained in the same manner as in Example 1 except that the washing step of washing a crude HPMCAS was not carried out. The HPMCAS suspension was subjected to liquid removal (solid-liquid separation) by using a centrifugal decanter (decanter type continuous centrifugal separator, type Z18, manufactured by TANABE WILLTEC INC.) at a centrifugal effect of 2500 G. After the liquid removal, the HPMCAS particles had an average particle size of 213 μm and the reduction ratio was 18%. After the liquid removal, the HPMCAS cake had a liquid content of 64.7% by weight.

The HPMCAS cake was dried at 80° C. in the same manner as in Example 1. The drying time of the HPMCAS cake was 0.75 relative to the drying time of the liquid-removed HPMCAS cake in Comparative Example 1 after liquid removal by using a filtration type centrifugal dehydrator. The results are shown in Table 1.

The dried HPMCAS was then sieved through a 10-mesh sieve (sieve opening of 1700 μm), and the average particle size by dry laser diffractometry was determined to be 190 μm, which satisfied an intended average particle size of 100 to 200 μm. The result is shown in Table 2.

Various powder properties of the HPMCAS after sieving were determined, and the results are shown in Table 2.

Comparative Example 2

The HPMCAS in Comparative Example 1 was pulverized with an impact mill (Victory Mill, type VP-1, manufactured by Hosokawa Micron Corporation) to obtain HPMCAS having an average particle size of 283 μm. Various powder properties of the HPMCAS after sieving were determined, and the results are shown in Table 2.

Comparative Example 3

The HPMCAS in Comparative Example 1 was pulverized with an impact type pulverizer (type ACM-10, manufactured by Hosokawa Micron Corporation) to obtain HPMCAS having an average particle size of 152 μm. Various powder properties of the HPMCAS after sieving were determined, and the results are shown in Table 2.

TABLE 1

| | suspension temp. (° C.) | suspension conc. (wt %) | average particle size before liquid removal (μm) | centrifugal effect G (—) | average particle size after liquid removal (μm) | reduction ratio of average particle size (%) | liquid content after liquid removal (wt %) | relative drying time (—) |
|---|---|---|---|---|---|---|---|---|
| Example 1 | 13 | 6 | 615 | 2500 | 178 | 71 | 65.1 | 0.68 |
| Example 2 | 13 | 6 | 615 | 900 | 343 | 44 | 66.4 | 0.95 |
| Example 3 | 13 | 6 | 494 | 2500 | 196 | 60 | 64.9 | 0.72 |
| Example 4 | 13 | 6 | 209 | 2500 | 149 | 29 | 64.2 | 0.63 |
| Example 5 | 13 | 6 | 260 | 2500 | 213 | 18 | 64.7 | 0.75 |
| Comp. Ex. 1 | 13 | 6 | 615 | 1200 | 596 | 3 | 66.0 | 1.00 |

TABLE 2

| | average particle size (μm) | loose bulk density (g/cm$^3$) | tapped bulk density (g/cm$^3$) | compressibility (%) | repose angle (°) |
|---|---|---|---|---|---|
| Example 1 | 160 | 0.338 | 0.422 | 19.9 | 37.8 |
| Example 2 | 295 | 0.359 | 0.435 | 17.5 | 36.4 |
| Example 3 | 174 | 0.342 | 0.411 | 16.8 | 36.9 |
| Example 4 | 131 | 0.331 | 0.390 | 15.1 | 38.1 |
| Example 5 | 190 | 0.349 | 0.428 | 18.5 | 36.8 |
| Comp. Ex. 1 | 477 | 0.371 | 0.419 | 11.5 | 36.3 |
| Comp. Ex. 2 | 283 | 0.351 | 0.446 | 21.3 | 37.0 |
| Comp. Ex. 3 | 152 | 0.324 | 0.454 | 28.6 | 37.7 |

Each HPMCAS in Examples had an intended average particle size and had excellent flowability. In contrast, the HPMCAS in Comparative Example 1 had a larger average particle size than the intended size, and the HPMCASs in Comparative Examples 2 and 3, which were obtained by pulverizing the HPMCAS in Comparative Example 1, had poor flowability.

The invention claimed is:

1. A method for producing hypromellose acetate succinate, comprising:

an esterification step of reacting hypromellose with esterification agents in the presence of a catalyst to obtain a reaction solution containing crude hypromellose acetate succinate;

a precipitation step of mixing the reaction solution with water to precipitate the crude hypromellose acetate succinate, thereby obtaining a hypromellose acetate succinate suspension;

a liquid removal step of removing a liquid from the hypromellose acetate succinate suspension with a centrifugal decanter to obtain liquid-removed hypromellose acetate succinate; and a drying step of drying the liquid-removed hypromellose acetate succinate, wherein in the liquid removal step, an average particle size, determined by a sieve analysis, is reduced by, or has a reduction ratio of, 10 to 90% with the centrifugal decanter and without using a pulverizer, and wherein the centrifugal decanter comprises an outer rotary cylinder having a substantially cylindrical shape with a small inner diameter at one of the longitudinal direction ends of the cylinder, and being rotatable at a high speed, and a screw conveyor concentrically provided inside the outer rotary cylinder, wherein the outer rotary cylinder comprises a discharge port for discharging a separated solid at one end with a small inner diameter in the longitudinal direction of the cylinder to the outside of the centrifugal decanter; and a drainage port for draining a separated liquid at the other end in the longitudinal direction of the cylinder to the outside of the centrifugal decanter; and wherein the solid settled on the inner wall of the outer rotary cylinder sequentially moves in the direction of the discharge port by the screw conveyor, undergoes liquid removal by centrifugal force on a slope toward the discharge port, and is discharged through the discharge port to an outside of the centrifugal decanter; and the centrifugal decanter in operation provides a centrifugal effect of 500 G or more, where the centrifugal effect is an index indicating the intensity of centrifugal force applied to a suspension, and is defined by the following equation:

$$\text{Centrifugal effect } G(-)=N^2\cdot r/894,$$

wherein N is the number of rotations per minute of an outer rotary cylinder, and r is an inner radius (unit: m) of the outer rotary cylinder.

2. The method for producing hypromellose acetate succinate according to claim 1, further comprising, between the precipitation step and the liquid removal step, a washing step of washing the crude hypromellose acetate succinate.

3. The method for producing hypromellose acetate succinate according to claim 1, wherein the liquid-removed hypromellose acetate succinate has an average particle size, determined by a sieve analysis, of 70 to 400 μm.

4. The method for producing hypromellose acetate succinate according to claim 1, wherein suspended particles in the hypromellose acetate succinate suspension to be fed to the centrifugal decanter have an average particle size, determined by a sieve analysis, of 150 μm or more.

5. The method for producing hypromellose acetate succinate according to claim 4, wherein when the suspended particles have an average particle size, determined by a sieve analysis, of 150 to 300 μm, the reduction ratio is 10 to 30%.

6. The method for producing hypromellose acetate succinate according to claim 4, wherein when the suspended particles have an average particle size, determined by a sieve analysis, of 300 μm or more, the reduction ratio is 30 to 90%.

7. The method for producing hypromellose acetate succinate according to claim 1, wherein the reduction ratio is 20 to 80%.

8. The method for producing hypromellose acetate succinate according to claim 1, wherein the liquid-removed hypromellose acetate succinate has an average particle size, determined by a sieve analysis, of 80 to 350 μm.

9. The method for producing hypromellose acetate succinate according to claim 1, wherein the liquid-removed hypromellose acetate succinate has an average particle size, determined by a sieve analysis, of 100 to 300 μm.

10. The method for producing hypromellose acetate succinate according to claim 1, wherein the hypromellose acetate succinate has an average particle size, determined by dry laser diffractometry, of 70 to 300 μm and a compressibility of 20% or less.

11. The method for producing hypromellose acetate succinate according to claim 1, wherein the hypromellose acetate succinate has an average particle size, determined by dry laser diffractometry, of 70 to 250 μm and a compressibility of 18% or less.

12. The method for producing hypromellose acetate succinate according to claim 11, wherein the compressibility is 0%.

13. The method for producing hypromellose acetate succinate according to claim 1, wherein the hypromellose acetate succinate has a loose bulk density of 0.1 to 0.6 g/cm$^3$.

14. The method for producing hypromellose acetate succinate according to claim 1, wherein the hypromellose acetate succinate has a packed bulk density of 0.1 to 0.7 g/cm$^3$.

15. The method for producing hypromellose acetate succinate according to claim 1, wherein the hypromellose acetate succinate has a repose angle of 45° or less.

16. The method for producing hypromellose acetate succinate according to claim 1, wherein the hypromellose acetate succinate has a repose angle of 40° or less.

* * * * *